United States Patent [19]

Brunet et al.

[11] Patent Number: 5,127,548
[45] Date of Patent: Jul. 7, 1992

[54] MEDICINAL SPRAY DEVICE WITH TWO SUBSTANCE COMPARTMENTS SEPARATED BY PUNCTURABLE MEMBRANE

[75] Inventors: Michel Brunet, Sainte-Colombe-la-Commanderie; Claude Jouillat, Montigny-sur-Avre, both of France

[73] Assignee: Valois, Le Neubourg, France

[21] Appl. No.: 658,611

[22] Filed: Feb. 21, 1991

[30] Foreign Application Priority Data

Feb. 21, 1990 [FR] France ................... 90 02130

[51] Int. Cl.⁵ .............................................. B67D 5/00
[52] U.S. Cl. ...................................... 222/80; 222/145; 222/260
[58] Field of Search ................... 222/94, 80-83, 222/129, 136, 145, 320, 321, 383, 385, 386, 401, 402.1, 402.2, 402.24, 653, 260; 206/222; 604/82, 87, 98, 92, 140, 205

[56] References Cited

U.S. PATENT DOCUMENTS 3,370,754 12/1966 Cook et al. ...................... 222/136
3,756,390 9/1973 Abbey et al. ..................... 604/87
4,693,706 9/1987 Ennis, III .......................... 604/87

Primary Examiner—Michael S. Huppert
Assistant Examiner—Philippe Derakshani
Attorney, Agent, or Firm—Sughrue, Mion, Zinn Macpeak & Seas

[57] ABSTRACT

A device for administering a medicine in the form of a spray, the medicine being constituted by a mixture of at least two substances that must be stored separately prior to use, the device comprising a volume which is divided into two compartments by a membrane 2 suitable for puncturing or tearing. The volume is defined by a receptacle 1A, 1B which is generally tubular in shape, and which is open at both ends. A suction and spray pump 4 is crimped onto one end thereof while its opposite end has a free piston 6 slidably received in the tubular element 1B to reduce the inside volume thereof as the pump sucks the content out from the tubular element after the membrane has been punctured.

14 Claims, 2 Drawing Sheets

MEDICINAL SPRAY DEVICE WITH TWO SUBSTANCE COMPARTMENTS SEPARATED BY PUNCTURABLE MEMBRANE

The present invention relates to a device for administering medicine in the form of a spray, the medicine being constituted by a mixture of at least two substances which need to be stored separately within the device until shortly before use.

BACKGROUND OF THE INVENTION

Devices of this nature exist for administering medicines, which devices are organized to store two substances separately and to mix them at the moment of use. Some such devices include a receptacle which is separated into two compartments by a membrane, together with means for tearing or perforating the membrane in order to mix the two substances.

SUMMARY OF THE INVENTION

The present invention provides a device of this type which is remarkable in that it includes a tubular element open at both ends and separated into two compartments by a perforable membrane, one end of the tubular element having a suction and spray pump crimped thereon while its other end has a piston free to slide inside the tubular element so as to reduce its inside volume as and when the pump sucks out the contents from the tubular elements, with the inside face of the piston being provided with projections for perforating the membrane.

Advantageously, the tubular element has two different diameters separated by a step against which the membrane is fixed. The pump is preferably crimped to the smaller diameter portion.

BRIEF DESCRIPTION OF THE DRAWING

An embodiment of the invention is described by way of example with reference to the accompanying drawing, in which.

DETAILED DESCRIPTION

Figure 1:
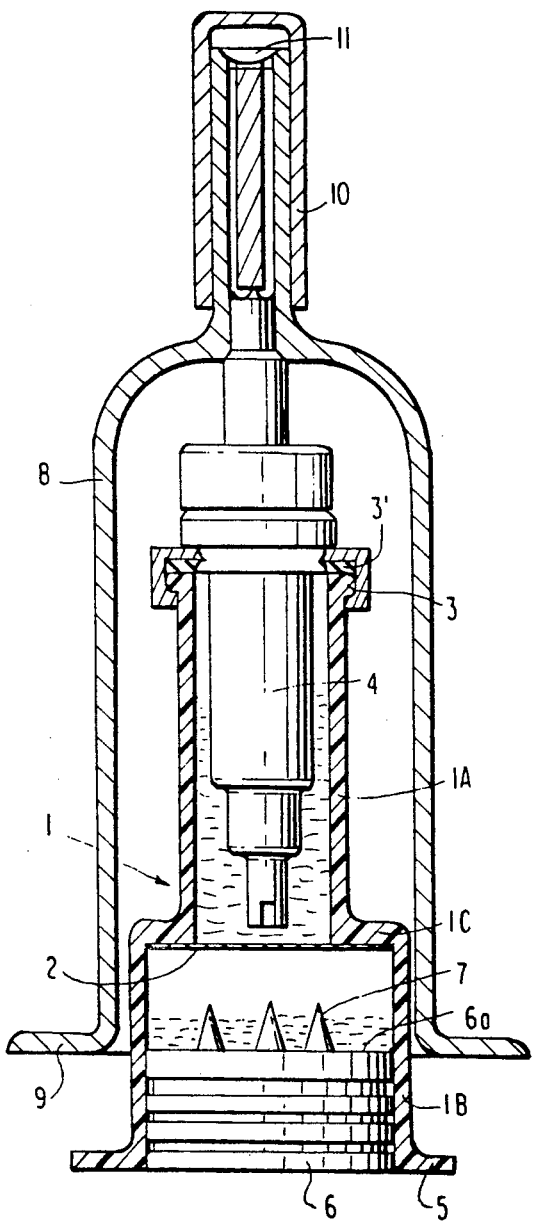
FIG. 1 is a fragmentary section view through a device of the invention in which two substances are kept out of contact with each.

The embodiment shown in FIG. 1 comprises a receptacle 1 in the form of two different-diameter tubes 1A and 1B interconnected by a step-forming annulus 1C. This component may be made of glass or of plastic and it may be transparent or opaque. A liquid-tight membrane 2 lies in the plane of the step 1C and is fixed in liquid-tight manner around its perimeter by any suitable means such as gluing, welding, heat sealing, etc. ... and it is made of a material that is relatively easy to tear or puncture.

The end of the small diameter portion 1A has a flange 3 onto which a suction and spray pump 4 is crimped over an interposed gasket 3'. The pump extends inside the portion 1A to the vicinity of the membrane 2.

The end of the larger diameter portion 1B is formed with an outwardly directed collar 5 to facilitate handling the device and to exert the pressure required to operate the pump. A free piston 6 is disposed inside the larger diameter portion and the axial thickness of the piston is sufficient to guide it. The piston is formed with appropriate ribs and grooves for providing sealing against the cylindrical wall of the portion 1B of the receptacle. The piston 6 has a face 6a facing towards the inside of the receptacle, i.e. towards the step 1C. Projections such as spikes 7 are provided on this face 6a facing the section of the smaller diameter portion 1A for the purpose of puncturing and/or tearing the membrane by pushing home the piston.

The pump is provided with a pusher 8 having fins 9 to enable the pump to be actuated by moving the fins 9 towards the collar 5. A cap 10 protects the outlet orifice 11 of the pump. The pump is of the "airless" type. Since the substances are pharmaceutical products it is preferable or even essential to avoid pollution from any air that could be admitted and come into contact with the substances contained in the receptacle. The pump can therefore not be operated without the membrane 2 being pierced. However, in the absence of a membrane or once it has been punctured or torn, each time the pump is actuated to suck fluid from the inside volume of the receptacle, atmospheric pressure acting on the free outside face of the piston causes the piston to move towards the pump until it comes into abutment against the step 1C.

The device of the invention is thus filled before use with two different substances or mixtures of substances on opposite sides of the membrane. The device is then in the position shown in FIG. 1. It is thus possible for two substances that should not be mixed together too long before use to coexist inside the device. At least one of the two substances is a liquid. The other may also be a liquid, or it may be a solid (powder or lyophilizate) suitable for being conveyed in solution or in suspension in the liquid. In order to mix the two substances, the piston must be pushed home so that its spikes 7 tear the membrane 2. To do this, the piston must be moved and to allow the piston to move the contents of the portion 1B of the receptacle must not be incompressible, i.e. it must contain a gas, air or nitrogen depending on circumstances (risk of oxidization), and sterilized if necessary. To facilitate the operation, gas may also be provided in portion 1A of the receptacle.

Figure 2:
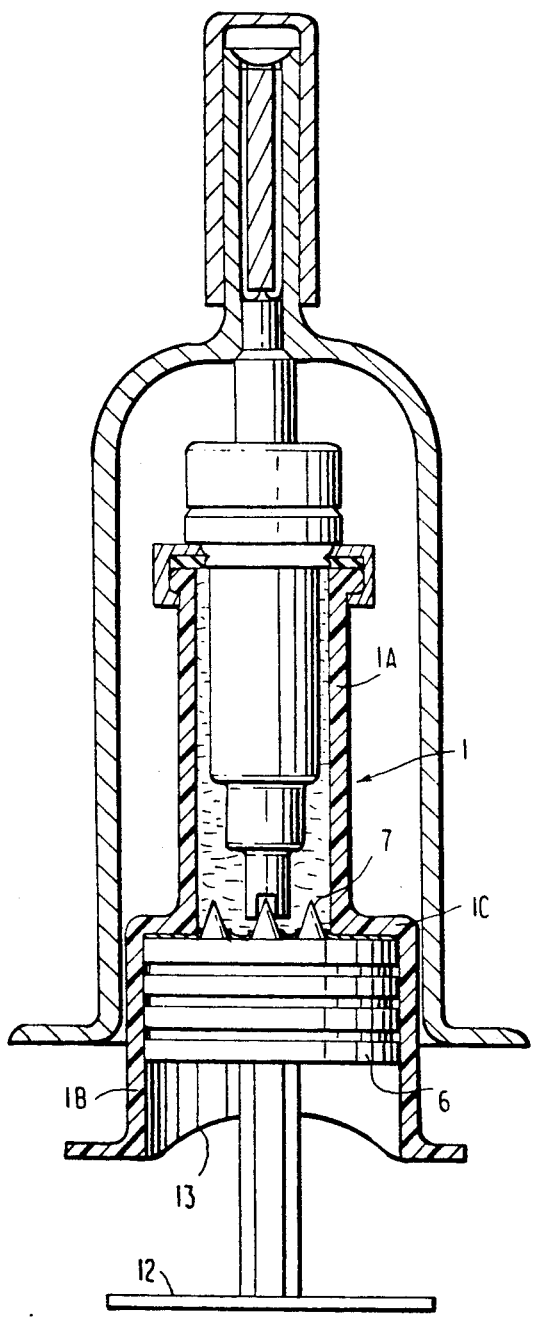
FIG. 2 is a view similar to FIG. 1 after the two substances have been mixed together.

FIG. 2 shows one way in which the mixing operation may be performed. The piston 6 is pushed in initially so that its spikes 7 perforate and tear the membrane 2. Some of the liquid contained in receptacle portion 1A then passes into portion 1B. The device is then shaken to ensure that the contents of portion 1B is mixed, dissolved, put into suspension, or put into an emulsion. After such blending, the piston 6 is pushed home until it comes into abutment against the step 1C. This can only be done if a sufficient quantity of gas is provided in the two compartments of the receptacle. Mixing can then be completed. To facilitate this operation, a handle 12 may be used e.g. by being screwed into the piston which then includes a tapped recess to receive the rod on the handle. After this operation, the piston is pushed back by the compressed gas expanding and returns substantially to its initial position. The device is then ready for use. It may be observed that in order to facilitate handling, the outside end of receptacle portion 1B may be formed with a notch 13.

The embodiment of the invention shown in FIGS. 1 and 2 is particularly suitable for packaging a lyophilizate in receptacle portion 1B. To do this, after the membrane 2 has been put into place, the receptacle 1 is turned upsidedown, i.e. with its collar 5 uppermost, and then receptacle portion 1B is filled completely or partially with a substance to be freeze dried, and the piston 6 is partially engaged in said receptacle portion 1B in such a manner as to allow receptacle portion 1B to remain in communication with the outside via the notch 13. The substance to be freeze dried is then frozen followed by sudden heating under a vacuum, thereby causing the water contained in said substance to be sublimed and leaving a dry residue or lyophilizate. Thereafter the piston 6 can be fully engaged to take up the position shown in FIG. 1, thereby isolating the receptacle portion 1B, possibly after filling said portion 1B with a gas, e.g. nitrogen. When receptacle portion 1B contains a lyophilizate, it is particularly advantageous for the membrane 2 to be a metal membrane or to be formed of a material which is a good conductor of heat so as to improve heat exchange during freezing and subliming.

Each of the two compartments may contain a plurality of substances, i.e. a mixture. The object of the device is merely to provide for the situation where there are at least two substances amongst the substances constituting a medicine that must not be together for long before use.

Figure 3:
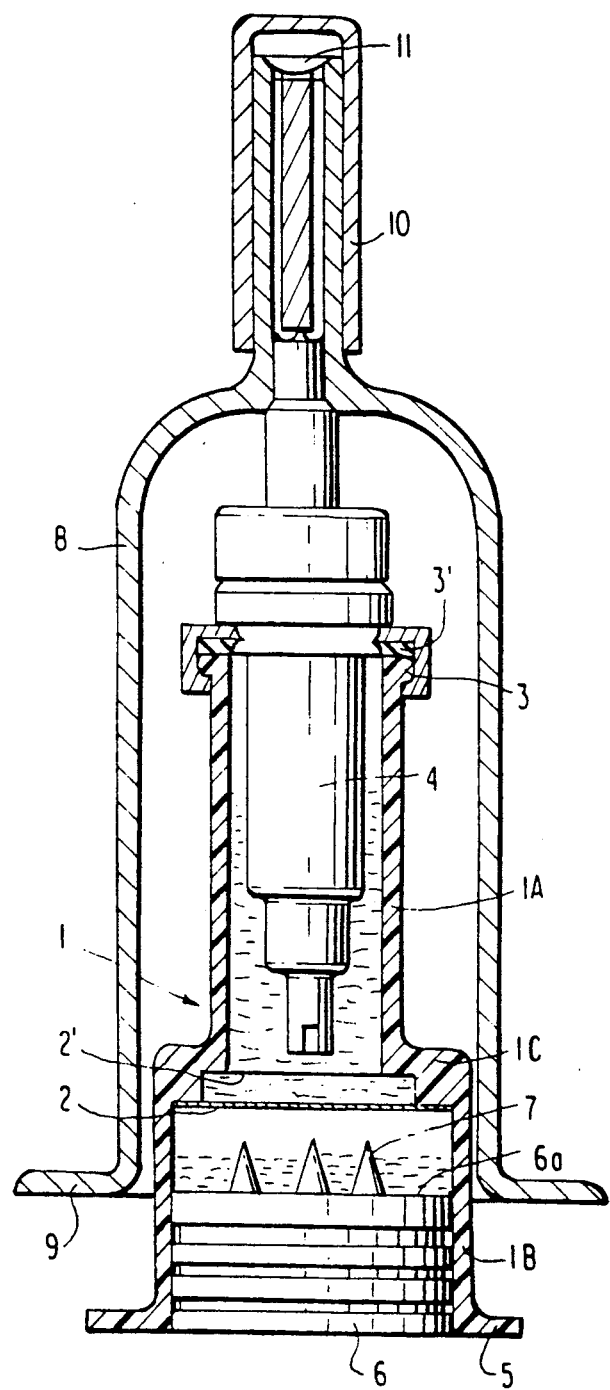
FIG. 3 is a view similar to FIG. 1, showing an alternative construction.

The same principle may be applied to more than two substances by having a plurality of membranes in parallel providing that the spikes on the piston can puncture all of them. It is also possible to provide a plurality of steps in order to improve the conditions under which membranes are fixed. Thus, FIG. 3 shows an embodiment of the invention having two parallel, tearable or puncturable membranes 2 and 2'. In this particular example, each membrane has its periphery fixed to a strep of the receptacle 1.

We claim:

1. A device for administering a medicine in the form of a spray, the medicine being constituted by a mixture of at least two substances that must be stored separately prior to use, the device comprising: a receptacle which is generally tubular in shape open at both ends, and divided into two compartments by a membrane capable of being punctured, a suction and spray pump crimped onto one end of the receptacle, a free piston disposed in another, opposite end of the receptacle, the piston including puncture means for perforating the membrane when the piston is pushed in, said piston being slidable in the tubular receptacle to reduce an inside volume thereof as the pump sucks out a content of the tubular receptacle after the membrane has been punctured.

2. A device according to claim 1, wherein the suction and spray pump comprises an "airless" pump.

3. A device according to claim 1, wherein the tubular receptacle contains a sufficient quantity of gas to enable the piston to be pushed in as far as a plane of the membrane to enable both substances to be thoroughly mixed.

4. A device according to claim 1, wherein said another, opposite end of the receptacle is formed with a notch.

5. A device according to claim 1, wherein an outside face of the piston includes a tapped cavity for receiving a handle to facilitate pushing in the piston and perforating the membrane.

6. A device according to claim 1, wherein said one end of the receptacle is formed with a flange onto which the pump is fixed by crimping.

7. A device according to claim 1, wherein said another end of the receptacle is formed with a collar to facilitate handling of the device.

8. A device according to claim 1, wherein at least one of the compartments is subdivided by at least one further membrane.

9. A device according to claim 8, wherein the receptacle includes a plurality of steps.

10. A device according to claim 1, wherein the receptacle is made of glass.

11. A device according to claim 1, wherein the receptacle is made of plastic.

12. A device according to claim 4, wherein the membrane is constituted by a material which is a good conductor of heat.

13. A device according to claim 1, wherein the receptacle is stepped at a position of the membrane, and the two compartments have different diameters.

14. A device according to claim 1, wherein the puncture means comprises spikes.

* * * * *